(12) United States Patent
Holopainen

(10) Patent No.: US 12,428,535 B2
(45) Date of Patent: Sep. 30, 2025

(54) HIGH THROUGHPUT MANUFACTURE OF POLYURETHANE FOAM LAYERS

(71) Applicant: Mölnlycke Health Care AB, Gothenburg (SE)

(72) Inventor: Antti Tapani Holopainen, Mikkeli (FI)

(73) Assignee: Mölnlycke Health Care AB, Möndal (SE)

( * ) Notice: Subject to any disclaimer, the term of this patent is extended or adjusted under 35 U.S.C. 154(b) by 950 days.

(21) Appl. No.: 17/621,312

(22) PCT Filed: Jun. 22, 2020

(86) PCT No.: PCT/EP2020/067325
§ 371 (c)(1),
(2) Date: Dec. 21, 2021

(87) PCT Pub. No.: WO2020/260191
PCT Pub. Date: Dec. 30, 2020

(65) Prior Publication Data
US 2022/0356318 A1  Nov. 10, 2022

(30) Foreign Application Priority Data
Jun. 24, 2019 (EP) .................... 19182009

(51) Int. Cl.
*C08J 9/02* (2006.01)
*A61L 15/26* (2006.01)
*A61L 15/42* (2006.01)

(52) U.S. Cl.
CPC ............. *C08J 9/02* (2013.01); *A61L 15/26* (2013.01); *A61L 15/425* (2013.01); *C08J 2207/10* (2013.01); *C08J 2375/06* (2013.01)

(58) Field of Classification Search
CPC ............. A61L 15/425; C08J 2207/10; B29C 2035/0822
See application file for complete search history.

(56) References Cited

U.S. PATENT DOCUMENTS

| 5,182,313 | A | * | 1/1993 | Carson ............. B29C 44/588 249/117 |
| 5,254,301 | A | | 10/1993 | Sessions et al. |
| 9,168,324 | B2 | * | 10/2015 | Mager ............. C08G 18/4833 |
| 2014/0295134 | A1 | | 10/2014 | Wood et al. |
| 2015/0011666 | A1 | | 1/2015 | McEvoy |
| 2019/0083675 | A1 | | 3/2019 | Carr et al. |

FOREIGN PATENT DOCUMENTS

| EP | 305175 A * | 3/1989 | ............. A61L 15/58 |
| EP | 0305175 A1 | 3/1989 | |
| EP | 2175896 A1 | 4/2010 | |

OTHER PUBLICATIONS

International Search Report and Written Opinion were mailed on Sep. 21, 2020 by the International Searching Authority for International Application No. PCT/EP2020/067325 filed on Jun. 22, 2020 and published as WO 2020/260191A1 (Applicant—Molnlycke Health Care AB) (16 pages).

\* cited by examiner

*Primary Examiner* — Andrew S Rosenthal
(74) *Attorney, Agent, or Firm* — Ballard Spahr LLP

(57) ABSTRACT

Described is an at least partly continuous process for making polyurethane foam layers that are suitable for medical applications, in particular in wound dressings, at a high throughput rate. The described process includes a step of accelerated curing of the polyurethane foam performed at a stage of the overall curing process at which the risk of a run-away reaction is minimized.

14 Claims, 3 Drawing Sheets

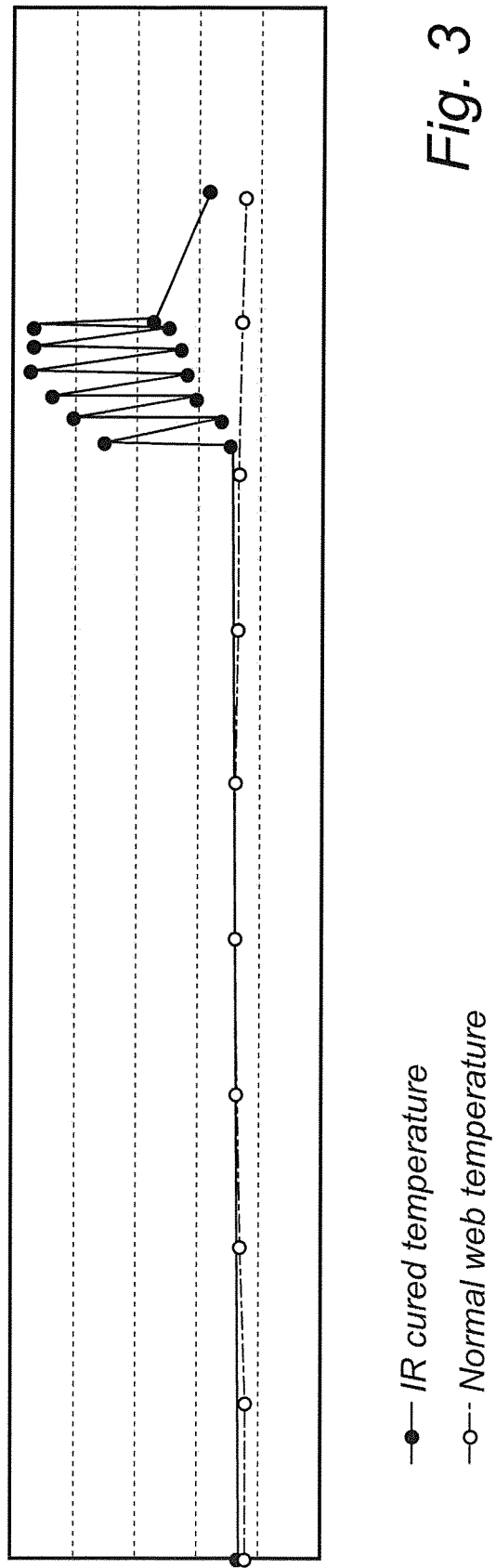

HIGH THROUGHPUT MANUFACTURE OF POLYURETHANE FOAM LAYERS

CROSS-REFERENCE TO RELATED APPLICATIONS

This application is a U.S. National Phase Application of International Application No. PCT/EP2020/067325, filed Jun. 22, 2020, which claims priority to European Application No. 19182009.1, filed Jun. 24, 2019, each of which are hereby incorporated by reference in their entirety.

FIELD OF THE INVENTION

The present invention relates to an at least partly continuous high throughput process for making polyurethane foam layers that are suitable for medical applications, in particular in wound dressings. Said process comprises a step of accelerated curing of the PU foam performed at a stage of the overall curing process at which the risk of a run-away reaction is minimized.

BACKGROUND OF THE INVENTION

Wound dressings are used to heal and protect wounds. The capability of the wound dressing to absorb and retain exudate from the wound is of paramount importance for the healing process. The liquid handling capacity of a dressing also affects the frequency of dressing changes, which should be minimized to promote wound healing. In particular, hydrophilic materials are used in wound dressing to absorb and retain wound fluids, further particularly hydrophilic foams such as hydrophilic open-cell polyurethane (PU) foams.

Processes for making PU foams that are particularly suitable for medical applications are known from the art, for example from U.S. Pat. No. 5,254,301, which discloses a continuous process for making polymer-based foam sheet, in a particular an isocyanate capped polyether-based foam. The process is specifically conducted at room temperature and the thickness of the layer is adjusted by way of a foam compression step applied during curing. The fact that the process is conducted at room temperature means that heat for further activating the curing process only stems from the exothermic reaction. Conducting the curing of PU foams, in particular TDI-based foams at room temperature and not increasing the curing rate by increasing the temperature from the outside is due to the fact that the curing/crosslinking reaction for these foams is easily accelerated beyond control.

Another process for making hydrophilic foams is described in US 2019/0083675, which discloses a process for making a multilayer foam comprising a polyurethane foam matrix. A reactive prepolymer mixture is deposited onto a (first) foam layer substrate and the reaction product is allowed to rise. In order to adjust a desired final thickness, the foam layer is compressed during the curing step.

The processes for making PU foams as known from the art generally require either full batch processing (see, e.g. US 2015/0011666) and/or relatively large production lines and/or are associated with comparatively low line speeds. Comparatively low line speeds are generally seen as required, in particular, for reactive prepolymer mixtures (such as mixtures comprising TDIs) since lower line speeds increase the residence time of a given foam segment in the production line (for example prior to drying and/or storage) and therefore allows the foam layers to fully (or to at least sufficiently) cure.

SUMMARY OF THE INVENTION

Based on the prior art and background as discussed above, there is a need in the art to provide a process for making polyurethane foams which process allows for a higher throughput of foam, in particular for the production of foam suitable for medical application, within a shorter time interval than generally achievable in processes known from the art. Such a process should avoid or minimize at least one of the disadvantages known from the processes in the art and should allow for improved process control, in particular avoiding or minimizing "runaway" curing/cross-linking reactions, while still allowing for high throughput processing.

According to a first aspect of the invention, these and other objects are achieved through a process for making a polyurethane foam layer, wherein said process comprises at least the following steps:
  (i) at least one mixing step in which one or more polyurethane prepolymer(s) or precursor(s) thereof is/are mixed or brought in contact, with each other, and/or with another component, in a mixing or contact zone;
  (ii) at least one layer forming step in which the mixture from step (i) is applied onto a moving substrate in a manner as to form a layer, and to begin the curing process on the substrate;
  (iii) at least one transporting step during which the foam layer on the substrate from step (ii) is a least partly moved along a production line, during which step the polyurethane prepolymer or precursor thereof in the foam layer at least partly cures, and the thickness of the layer increases due to foaming, i.e. due to a least one chemical reaction occurring within the layer;
  (iv) at least one step of accelerated curing, which occurs at a predetermined point in time after conclusion of step (ii) or, correspondingly, at a predetermined location along the production line, wherein curing is accelerated by subjecting the foam as moving on the substrate to radiation heating, preferably to infrared radiation.

In embodiments of the invention, the process comprises the following additional step, which is implemented after step (iv):
  (v) separately from and after conclusion of step (iv): at least one drying step during which the essentially cured wet foam from step (iv) is dried to reach a predetermined lower water content.

In preferred embodiments, the essentially cured wet foam comprises at least 10% w/w of water, preferably at least 30% w/w of water, further preferably at least 50% w/w of water and is dried to reach a predetermined water content equal to or less than 10% w/w, preferably less than 5% w/w, further preferably less than 2% w/w.

Prepolymers of Step (i)

In the mixing or contacting step (i), one or more prepolymer(s) or precursor(s) thereof may be mixed with itself or with other components. The other component may, in particular, be a solvent, in particular a protic solvent, further particularly water. The other component may also or in addition be another precursor or polymer.

Mixing of two or more components, in particular precursors that make up a prepolymer or that are quickly mixed together in a so-called "One Shot Technique" are also included.

In embodiments of the invention, the mixing or contacting step (i) is or includes a step of mixing at least one prepolymer with water.

No limitations exist in regard to the prepolymers, precursors or in regard to any other component added, or in regard to the overall mixture used in step (i) as long as the mixture leads to a polyurethane foam that is suitable for use in a medical dressing.

In accordance with the present invention, the term "prepolymer" is to be understood as defined in IUPAC: Compendium of Chemical Terminology, 2nd ed. (the "Gold Book"), compiled by A. D. McNaught and A. Wilkinson. Blackwell Scientific Publications, Oxford (1997), ISBN 0-9678550-9-8, as generally referring to a polymer or oligomer the molecules of which are capable of entering, through reactive groups, into further polymerization and thereby contributing more than one structural unit to at least one type of chain of the final polymer.

In embodiments of the invention, prepolymers may comprise or are isocyanate-capped polyols or isocyanate-capped polyurethanes.

In embodiments of the invention, the prepolymer derives from a reaction between a polyol and a diisocyanate compound, wherein said diisocyanate compound is selected from the group consisting of hexamethylene diisocyanate (HDI), toluene diisocyanate (TDI), methylene diphenyl diisocyanate (MDI), or isophorone diisocyanate (IPDI), or any mixture thereof.

Toluene diisocyanates (TDI) or mixtures comprising TDI are generally preferred for applications in medical dressings due to their improved performance as hydrophilic polyurethane foams.

Other Compounds of the Mixture of Step (i):

No restrictions exist in regard to the presence of other compounds or components in the prepolymer or precursor mixture of step (i) as long as those other compounds or components do not render the resulting PU foam unsuitable for medical applications, in particular wound care applications.

Suitable components to be included in the mixture of step (i) are, for example, water (used as a solvent and/or as a "chemical" blowing agent), surfactants (wetting agents), catalysts, solvents (in addition to or other than water), blowing agents, chain extenders, hydrophilic agents, cross-linking agents, pigments, filler particles, adjuvants, additional polymer components etc.

In embodiments of the invention, the mixture further comprises at least one surfactant, preferably a non-ionic surfactant.

Step (ii): "Substrate" and Onset of Curing

Curing of a given prepolymer or precursor mixture, for example by chemical reaction between OH-groups of polyols and isocyanate groups of polyisocyanates, or by chemical reaction between water and isocyanate groups of the prepolymer (e.g. in a step of preparing an aqueous mixture comprising a prepolymer which includes the step of mixing a prepolymer composition comprising the prepolymer with water) will typically begin the moment at which at least two components mixture are put into contact with each other, i.e. already in step (i), or even earlier. However for the purposes of timing of the curing process in accordance with the present invention, the "beginning" of the curing process is defined to be the moment at which a given volume segment of the prepolymer or precursor mixture from step (i) is applied onto the moving substrate in step (ii).

The term "cure" as used in accordance with the present invention, in particular, includes the formation of bonds between the polymers of the prepolymer in the mixture, in particular a cross-linking bond is or comprises urethane bond formed through reaction between an hydroxyl group on a first polymer and an isocyanate (NCO) group on a second polymer, or a urea bond formed through reaction between an amine group on a first polymer and an isocyanate (NCO) group on a second polymer.

In accordance with the present invention the term "curing" includes "cross-linking", i.e. cross-linking is one aspect, preferably the predominant effect of the overall curing process.

The term "cross-linked" is used herein to describe a material comprising a plurality polymeric molecules which are interlinked by a chemical bond, in particular a covalent bond or an ionic bond, or by a physical cross-link.

In embodiments of the invention, the prepolymers or precursors from step (i) as mixed or brought together are applied onto a moving substrate in a manner as to result in a given "coating weight" on the substrate ("coating weight"=grams of mixture dispensed per square centimeter of substrate). Said coating weight is suitably adapted to produce a desired final foam layer thickness. In embodiments of the invention, said grammage is from 30 $g/m^2$ to 1000 $g/m^2$, preferably from 50 $g/m^2$ to 500 $g/m^2$, further preferably from 75 $g/m^2$ to 250 $g/m^2$. These grammages generally correspond to film thicknesses that can be suitably penetrated by radiation, in particular IR radiation, as used in step (iv).

A "layer" as used in accordance with the present invention should be understood to have a continuous extension in one plane (x and y direction) and a thickness perpendicular to said plane (z direction). In accordance with the present invention, the length of the foam layer as ultimately resulting (typically as a rolled-up batch of dried and cured layer ready for storage) is greater by at least one order of magnitude than the width of the layer. The width of the layer is larger by at least a factor of 5 than the thickness of the layer.

No restrictions apply in regard to the specific realization of said moving substrate as long as said substrate is capable of accommodating the prepolymer or precursor mixture from step (i) without substantially reacting with the same (i.e. being essentially inert vis-à-vis the prepolymer/precursor mixture), and is capable of transporting a given volume segment of the prepolymer mixture along at least a part of the overall production line (i.e. translate the same at least in one direction) while the prepolymer mixture cures, and finally allows for the removal of the polyurethane foam as (essentially) cured or of the polyurethane foam as cured and dried.

In embodiments of the present invention, the substrate is realized as a moving conveyor belt, preferably as a moving web.

In other embodiments of the present invention, the substrate is realized as a moving release liner which is later removed ("sacrificial layer"). Suitable materials are silicone coated or fluoropolymer coated release liners. Silicone coated liners are preferred.

Furthermore, no restrictions apply in regard to how the mixture of step (i) is applied onto the substrate. Application through a nozzle is preferred. Further preferably, the nozzle is provided as a slit that defines an initial width and an initial thickness of the layer as present on the substrate In embodiments of the present invention, the initial thickness of the foam layer as applied on the substrate, i.e. at the beginning of step (ii) is from 100 µm to 8 mm, preferably from 250 µm to 2 mm.

Transporting Step (iii)

In embodiments of the present invention, a given volume segment of the foam is transported linearly by at least 3 m, preferably not less than 10 m, further preferably not less than 20 m in said transportation step (iii). Further preferred ranges are from 20 m to 80 m or 30 m to 50 m.

In embodiments of the present invention, a given volume segment of the foam is transported for from 36 seconds to 900 seconds, preferably for from 180 to 320 seconds, in said transportation step (iii).

Accelerated Curing Step (iv)

In embodiments of the present invention, the "predetermined point" in time of step (iv) at which point in time a given volume segment the foam layer as transported is subjected to heating by radiation may be determined by the thickness of the layer, the degree of curing or any other suitable parameter, in particular temperature. The reference point against which any of these predetermined points are measured is the onset of step (ii), i.e. the point in time and along the production line at which the prepolymers or precursors from step (i) as mixed or brought together and are applied onto the moving substrate.

In embodiments of the present invention, said "predetermined point" in time in step (iv) is reached when the thickness of the foam has increased by at least 60%, preferably at least 80% vis-à-vis the thickness of the layer as initially applied in step (ii) In embodiments of the present invention, said "predetermined point" in time in step (iv) is reached when the peak temperature of foam curing has been reached, preferably when the peak temperature has been passed, i.e. that the temperature has dropped or is starting to drop from the maximum.

In accordance with the present invention, the "peak temperature" is the highest or maximum temperature as measured on the surface of the foam, at a predetermined point in step (iii). Said temperature is suitably measured with an infrared temperature sensor.

In embodiments of the present invention, said "predetermined point" in time in step (iv) is reached when the temperature of the foam layer is in the range from 25° C. to 35° C., preferably from 27° C. to 32° C., after the temperature had been in the range of from 18° C. to 24° C., preferably from 18° C. to 23° C. at the beginning of step (iii).

In embodiments of the present invention, said "predetermined point" in time in step (iv) is reached 2 to 10 minutes after the beginning of step (iii), preferably 3 to 7 minutes after the beginning of step (iii).

In embodiments of the present invention, said "predetermined point" in time in step (iv) is reached once a given volume segment of the foam layer has reached a degree of curing of from 50% to 90%, preferably of form 65% to 85%.

The term "degree of curing" as used herein means the percentage of isocyanate groups that have reacted as measured by Fourier Transform Infrared Spectroscopy (FTIR), i.e. a 100% degree of curing means that essentially all isocyanate (NCO) groups have reacted, whereas 0% degree of curing means that essentially no isocyanate (NCO) groups have reacted.

The amount of NCO groups, and thus the corresponding degree of curing, at different stages of the method of producing the composite material can be monitored in situ (i.e. along the production line, for example by FTIR. The number of NCO groups corresponding to 0% degree of curing can be measured, i.e. calibration can be performed before the prepolymer/precursor components are mixed, in particular are mixed with water, i.e. prior to step (i).

The terms "completely cured" and "essentially completely cured" as used in accordance with the present invention mean a degree of curing of 90-100%.

Without wishing to be bound by theory, Applicants believe that the point of the overall curing process at which accelerated curing step (iv) is implement, the curing/crosslinking reaction has significantly abated and curing may be advantageously accelerated by way of homogenous energy input (i.e. energy input via radiation, in particular via IR radiation). By way of choosing homogeneous acceleration by radiation input and by way of choosing a point in time after which a significant part of the curing has already occurred, the risk of a "run-away" curing reaction, which may happen at an early stage of the overall curing process is minimized or avoided altogether.

In embodiments of the present invention, said "predetermined location" along the production line in step (iv) is 5 m or more from the point in the production line at which the mixture from step (i) is applied onto the substrate (i.e. "downstream"), preferably 10 m or more, further preferably 20 m or more.

In embodiments of the present invention, said "predetermined location" along the production line in step (iv) is in the downstream half of the production line [i.e. further down from the point in the production line at which the mixture from step (i) is applied onto the substrate], preferably in the last third of the production line.

In embodiments of the invention, the maximum temperature reached on the surface of the foam layer by way of the accelerated curing of step (iv) is controlled to be in the range of from 30° C. to 95° C., preferably from 45° C. to 90° C.

In embodiments of the invention, the zone of accelerated curing, i.e. the zone of step (iv) extends over a range of 1 m to 10 m of the overall production line, preferably over a range of from 2 m to 6 m.

In embodiment of the invention, accelerated curing is achieved by providing at least 2 IR lamps along the production line and being directed towards the moving foam layer, preferably by at least 4 IR lamps, further preferably by at least 6 IR lamps.

Without wishing to be bound by theory, Applicant believes that heating by radiation, in particular UV heating (in a wavelength range from 100 nm to 350 nm), IR heating (in a wavelength range from 700 nm to 1 mm) or heating by microwaves (in a wavelength range from 1 mm to 300 mm) is particularly advantageous for accelerating the chemical reactions underlying the curing process of a foam layer since this radiation is capable of at least partly penetrating the foam layer and then being absorbed inside the foam layer, thus accelerating chemical reaction by increasing temperature not only on or from the outside but also within and from the inside.

By contrast, conventional heating by convection or conduction as achieved by conventional heating means, for example in an oven, in which conventional heating the foam layer is brought into contact with hot air primarily increases the temperature from the outside and leads to temperature gradients. At a stage of the overall curing process at which curing has abated but not stopped or essentially stopped, introducing such a temperature gradient may lead to a gradient in curing along the width and length of the layer (more on the outside than the inside) which ultimately may lead to a non-homogeneously cured foam layer. Furthermore, conventional heating not only heats the foam but also the surrounding area, which needs to be heat controlled.

Therefore, in accordance with the present invention, heating by radiation allows to speed up the overall curing process while minimizing gradients in regard to the degree of curing along the thickness or width of the foam layer. Heating by radiation also allows to increase the response time vis-à-vis convection heating/heating by hot air/oven heating.

These advantages of acceleration by radiation apply, in particular for polyurethane-based foams since these are characterized by a relatively poor thermal conductivity.

In preferred embodiments of the invention, the accelerated curing of step (iv) is achieved by infrared heating with 2 or more, preferably 4 or more infrared lamps, further preferably by infrared heating with from 4 to 10 IR lamps. In further embodiments these lamps are spaced apart by between 20 cm and 2 meters, preferably between 40 cm and 100 cm. The inventors have found that by spacing the lamps not too closely, in particular by spacing the same in the distances indicated above, overheating of the curing foam can be avoided or minimized.

(v) Drying Step

In embodiment the present invention, the process comprises, after step (iv) a further and separate drying step (v).

Contrary to step (iv), the purpose of said drying step is not primarily to speed up curing ("post-curing" may still occur during said drying step), but rather to lower the water content in the foam layer.

In embodiments of the invention, the foam, has cured to a degree of at least 90%, preferably at least 95% o prior to drying step (v).

In preferred embodiments, the essentially cured wet foam comprises at least 10% w/w of water, preferably at least 30% w/w of water, further preferably at least 50% w/w of water and is dried to reach a predetermined water content equal to or less than 10% w/w, preferably less than 5% w/w, further preferably less than 2% w/w.

For foams used in medical applications, a residual water content of, for example, 5% w/w is generally seen as advantageous for foam performance.

In embodiment of the present invention, the temperature (maximum temperature or average temperature, or both) is lower in said drying step (v) than in the accelerated curing step (iv)

In embodiments of the present invention, in step (v) conventional heating by convection and/or conduction is used as the primary source of heat energy and no additional energy input by radiation is provided.

In embodiments of the invention, the maximum temperature reached by way of drying in step (v) is in the range of from 25° C. to 120° C., preferably from 50° C. to 75° C.

According to a second aspect of the invention, the above-mentioned and other objects are achieved by means of providing a wound dressing comprising the foam as obtained or obtainable by the process according to the invention.

In embodiments of the invention, the wound dressing comprises said foam layer, wherein said wound dressing further comprises at least one further layer, preferably a backing and/or an adhesive layer or coating, preferably two or more of these further layers.

General Definitions

In the claims, the terms "comprising" and "comprise(s)" do not exclude other elements or steps, and the indefinite article "a" or "an" does not exclude a plurality of elements or steps.

The mere fact that certain measures are recited in mutually different dependent claims does not indicate that a combination of these measured cannot be used to advantage.

BRIEF DESCRIPTION OF THE DRAWINGS

The above and other aspects of the invention will now be shown in more detail, also with reference to the appended drawings showing exemplary embodiments of the invention, wherein:

FIG. 3 shows a comparison of exemplary temperature profiles along the production line, showing the temperature profile (as a function of position along the production line shown in FIG. 1) of a foam on a substrate (here: web) according to conventional processing (no accelerated curing) and then according to an exemplary process of the present invention, using radiation heating by six IR lamps; the "spikes" in temperature are well discernible, but also that the temperature essentially returns to "normal" once IR heating is removed.

DESCRIPTION OF EMBODIMENTS OF THE INVENTION

Figure 1:
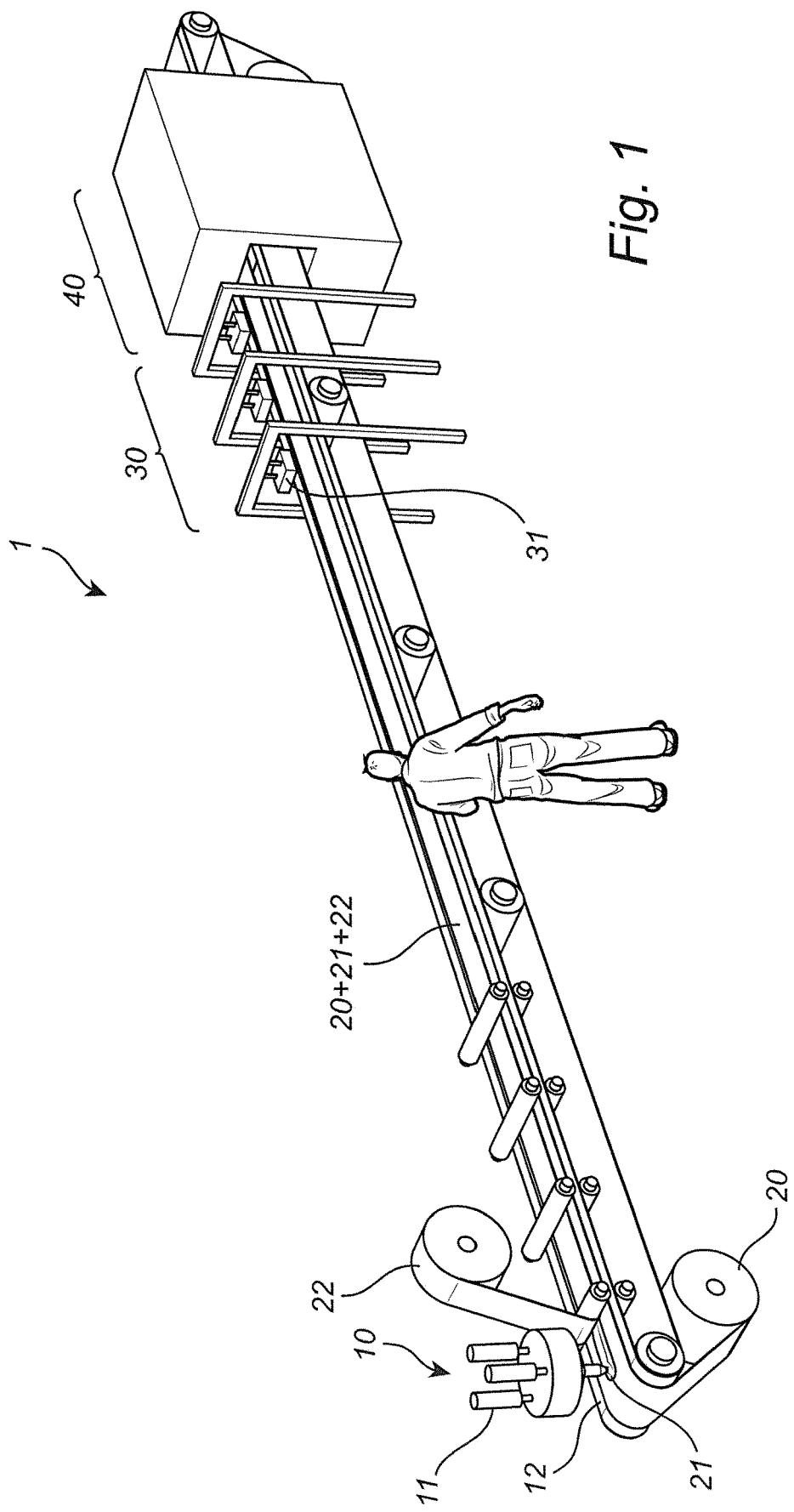
FIG. 1 shows a schematic and exemplary sketch of the overall production line (1), including a mixing chamber (10), here exemplarily shown with three feeding lines (11), a device for applying a foam layer, here realized exemplarily as nozzle (12) a substrate (20), here realized as a moving conveyor belt, onto which a foam layer (21) is dispensed from the nozzle, covered with an optional protective layer (22), a zone (30) for accelerated curing, here exemplarily equipped with three IR lamps (31), and a heating zone (40) for drying the foam.
Figure 2A:
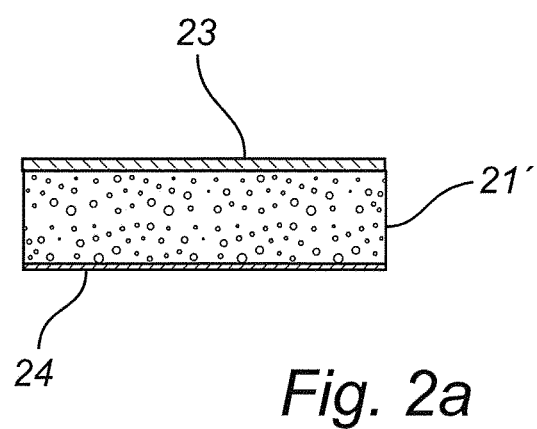
FIG. 2 shows an exemplary wound dressing employing a cured polyurethane foam (21') as made according to the process of the present invention, said wound dressing comprising a backing layer (23), said cured foam layer (21') and a wound contact layer (24).
In FIG. 2b, said wound contact layer is shown as a perforated wound contact layer (24').
Figure 2B:
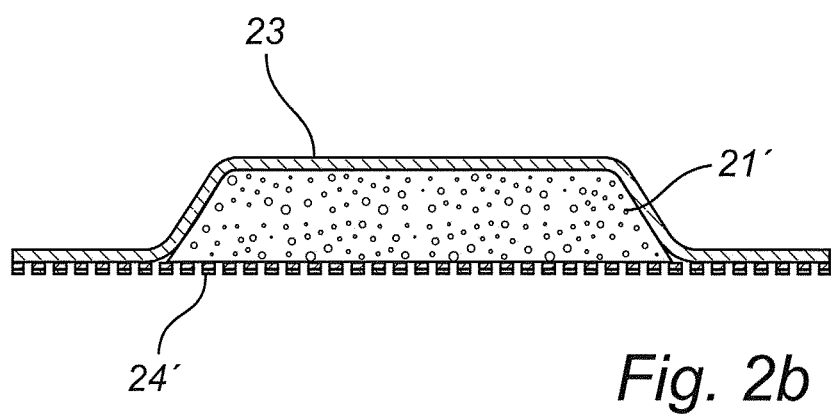

In the following further description, detailed embodiments of the present invention are described, with reference to the accompanying drawings, which are exemplary illustrations of embodiments of the invention.

Chemistry:

In embodiments of the invention, the prepolymer is or comprises an isocyanate-capped polyol or isocyanate-capped polyurethane.

In embodiments of the invention, the prepolymer derives from a reaction between a polyol and a diisocyanate compound selected from the group consisting of hexamethylene diisocyanate (HDI), toluene diisocyanate (TDI), methylene diphenyl diisocyanate (MDI), or isophorone diisocyanate (IPDI), or any mixture thereof.

In embodiments of the invention, the prepolymer derives from a reaction between a polyol, such a polyethylene glycol, and hexamethylene diisocyanate (HDI). In embodiments of the invention, the prepolymer is or comprises an hexamethylene isocyanate-capped polyol, preferably hexamethylene isocyanate-capped polyethylene glycol, or an hexamethylene isocyanate-capped polyurethane.

In preferred embodiments of the invention, the prepolymer derives from a reaction between a polyol and toluene diisocyanate (TDI). In embodiments of the invention, the prepolymer is or comprises a toluene isocyanate-capped polyol, preferably toluene isocyanate-capped polyethylene glycol, or a toluene isocyanate-capped polyurethane.

In embodiments of the invention, the prepolymer derives from a reaction between a polyol and methylene diphenyl diisocyanate (MDI). In embodiments of the invention, the prepolymer is or comprises a methylene diphenyl isocyanate-capped polyol, preferably methylene diphenyl isocyanate-capped polyethylene glycol, or a methylene diphenyl isocyanate-capped polyurethane.

In embodiments of the invention, said polyol is selected from the group consisting of polyester polyols, polyacrylate polyols, polyurethane polyols, polycarbonate polyols, polyether polyols, polyesterpolyacrylate polyols, polyurethane polyacrylate polyols, polyurethane polyester polyols, polyurethane polyether polyols, polyurethane polycarbonate polyols and polyester polycarbonate polyols, among others, in particular polycondensates of di or optionally tri-, and tetraols as well as di or optionally tri- and tetracarboxylic acids or hydroxycarboxylic acids or lactones.

Exemplary suitable diols are ethylene glycol, butylene glycol, diethylene glycol, triethylene glycol, polyalkylene glycols such as polyethylene glycol, and also 1,2-propanediol, 1,3-propanediol, 1,3-butanediol, 1,4-butanediol, 1,6-hexanediol and isomers, neopentyl glycol or neopentyl glycol hydroxypivalate, In addition, polyols such as trimethylolpropane, glycerol, erythritol, pentaerythritol, trimethylolbenzene or trishydroxyethyl isocyanurate are also within the scope of the present invention.

In embodiments of the invention, said polyol is a polyethylene glycol (polyethylene oxide). Accordingly, in embodiments of the invention, the prepolymer is or comprises an isocyanate-capped polyethylene glycol.

In embodiments of the invention, the content of the diisocyanate compound, in the prepolymer reaction mixture of the diisocyanate compound and the polyol, is at least 15% (w/w) (relative to the total weight of the diisocyanate and the polyol in the prepolymer reaction mixture). In embodiments of the invention, the content of the diisocyanate compound, in the prepolymer reaction mixture of the diisocyanate compound and the polyol, is 15-60%, preferably 20-50% (w/w).

Processing Conditions

In embodiments of the invention the overall process is performed in a manner so that the foam layer is processed at least partially continuously, in particular in or during steps (ii), (iii) and (iv).

"At least partially continuously" means that any batch-only or stationary processes are excluded. During the processing steps outlined above, the foam layer is transported, at least for part of the processing time, continuously along a production line.

In embodiments of the invention, the process overall is (only) partially continuous in that one defined volume of starting materials will ultimately result in a given number of foam rolls that may be stored and are used in further converting steps (e.g. to be coated with silicone and/or use as a layer in a wound pad, etc).

In embodiments of the invention, the process of the present invention is associated a temperature profile along the production line, wherein the highest overall temperature is achieved in accelerating step (iv).

Final Product

In embodiment of the invention the foam resulting after step (iv) or after step (v) is an open cell foam, in particular has at least 50% open pores, preferably at least 90% open pores. As used herein, the term "open-cell" refers to the pore structure of the foam, wherein the pores in an open-cell pore structure are connected to each other and form an interconnected network.

In embodiment of the invention the foam resulting after step (iv) or after step (v) is an open cell foam has pores having an average size that may vary from 30 µm to 1000 µm.

In accordance with the present invention the "average pore size" is to be understood as the (largest) cross-sectional area of the pore, wherein a spherical approximation of the pore is applied. The pore diameter is measured by image analysis of a cross-section of the foam material, wherein the image analysis method is based on ISO 13322-1:2014, and cross-sectional area of the pore is calculated accordingly.

In embodiments of the invention, the hydrophilic polyurethane foam layer resulting from step (iv) or from step (v) is an open-cell porous hydrophilic foam having a density of 60 to 180 kg/m$^3$ as measured according to standard method ISO 845:2006.

In embodiments of the invention, the foam layer is an open-cell porous hydrophilic foam having a density of 60 to 180 kg/m$^3$, preferably 100 to 150 kg/m$^3$, as measured according to standard method ISO 845:2006.

In embodiments of the invention the thickness of the foam as resulting from step (iv) or from step (v) is from 500 µm to 20 mm, preferably from 1 mm to 15 mm. In embodiments of the invention, the foam layer has a thickness of from 1 mm to 12 mm. In embodiments of the invention, the foam layer has a thickness of from 1 mm to 10 mm. In embodiments of the invention, the foam layer has a thickness of from 1 mm to 8 mm. In embodiments of the invention, the foam layer has a thickness of from 1 mm to 5 mm.

In embodiments of the present invention, the polyurethane foam layer resulting from step (iv) or from step (v) is hydrophilic.

In accordance with the present invention, the term 'hydrophilic' is to be understood as defined in IUPAC: Compendium of Chemical Terminology, 2nd ed. (the "Gold Book"), compiled by A. D. McNaught and A. Wilkinson. Blackwell Scientific Publications, Oxford (1997), ISBN 0-9678550-9-8, as generally referring to the capacity of a molecular entity or of a substituent to interact with polar solvents, in particular with water, or with other polar groups.

Preferably, the term 'hydrophilic' refers to the water-permeability property of a material or the water-attracting property of a molecule. In the context of a material with pores (here: open-cell foams) or materials with through-holes, such a material is 'hydrophilic' if the material wicks up water.

In embodiments of the invention, the foam material is characterized by a free swell absorptive capacity, corresponding to the maximum absorptive capacity, of from 800 to 2500 kg/m$^3$ as measured by EN 13726-1:2002.

In embodiments of the present invention, the polyurethane foam layer resulting from step (iv) or from step (v) has a speed of absorption of at least 5 µl/sec, preferably at least 10 µl/sec, more preferably at least 20 µl/sec.

Further Foam Components (Antimicrobial)

In embodiments of the invention, the foam layer comprises an antimicrobial agent. In embodiments of the invention, the antimicrobial agent comprises silver. In embodiments of the invention, the silver is metallic silver. In embodiments of the invention, the silver is a silver salt. In embodiments of the invention, the silver salt is silver sulfate, silver chloride, silver nitrate, silver sulfadiazine, silver carbonate, silver phosphate, silver lactate, silver bromide, silver acetate, silver citrate, silver CMC, silver oxide. In embodiments of the invention, the silver salt is silver sulfate. In embodiments of the invention, the antimicrobial agent comprises a monoguanide or biguanide. In embodiments of the invention, the monoguanide or biguanide is chlorhexidine digluconate, chlorhexidine diacetate, chlorhexidine dihydrochloride, polyhexamethylenebiguanide (PHMB) or a salt thereof, or polyhexamethylenemonoguanide (PHMG) or a salt thereof. In embodiments of the invention, the biguanide is PHMB or a salt thereof. In embodiments of the invention, the antimicrobial agent comprises a quaternary ammonium compound. In embodiments of the invention, the quaternary ammonium compound is cetylpyridinium chloride, benzethonium chloride, or poly-DADMAC. In embodiments of the invention, the antimicrobial agent comprises triclosan, sodium hypochlorite, copper, hydrogen peroxide, xylitol, or honey. The advantages of the present invention have been demonstrated in the following Examples.

EXAMPLES

Foam layers in accordance with embodiments of the invention were prepared at standard laboratory conditions (at room temperature unless otherwise stated).

A foam layer was prepared by the following steps: (1) an aqueous phase containing surfactants and commercially available Trepol® prepolymer from Rynel Inc. was metered to a mixer; (2) the aqueous and prepolymer were mixed in pin type mixer and dispensed in between 2 substrate layers; (3) the emulsion mixture was then molded in to thickness and width; (4) foam was freely cured on a moving conveyor running at a fixed line speed; (5). After approximately four minutes had passed, the reacting foam emulsion was heated with IR heaters (through the substrate layer) for approximately 0.5 minutes (24 seconds); (6) the web (substrate) then moved to the end of the conveyor, where the substrates were removed, exposing the foam to a drying step; in step (7), finished foam was collected into rolls and sampled.

This method in accordance with an exemplary embodiment of the present invention enabled approximately 25% faster cure time than an otherwise same or similar process without IR heaters. This advantage in process time was achieved while finding minimal to no effect on foam properties.

The invention claimed is:

1. Process for making polyurethane foam layer, said process comprising at least the following steps:
   (i) at least one mixing step in which one or more polyurethane prepolymer(s) comprising an isocyanate-capped polyol or an isocyanate-capped polyurethane is/are mixed or brought in contact, with each other, and with water, in a mixing or contact zone, wherein said polyurethane prepolymer derive(s) from a reaction between a polyol, and a diisocyanate compound selected from the group consisting of hexamethylene diisocyanate (HDI), toluene diisocyanate (TDI), methylene diphenyl diisocyanate (MDI), and isophorone diisocyanate (IPDI), or any mixture thereof;
   (ii) at least one layer forming step in which the mixture from step (i) is applied onto a moving substrate to form a layer and to begin the curing process on the substrate;
   (iii) at least one transporting step during which the foam layer on the substrate from step (ii) is a least partly moved along a production line, during which step the polyurethane prepolymer or precursor thereof in the foam layer at least partly cures, and the thickness of the layer increases due to foaming;
   (iv) at least one step of accelerated curing, which occurs at a predetermined point in time after conclusion of step (ii) and, correspondingly, at a predetermined location along the production line, wherein curing is accelerated by subjecting the foam as moving on the substrate to radiation heating,
   wherein said "predetermined point" in time in step (iv) is reached 2 to 10 minutes after the beginning of step (iii), or
   wherein said "predetermined point" in time in step (iv) is reached once a given volume segment of the foam layer has reached a degree of curing of from 50% to 90%.

2. Process according to claim 1, wherein said process comprises at least further step (v), which is implemented after step (iv):
   (v) separately from and after conclusion of step (iv): at least one drying step during which the essentially cured wet foam from step (iv) is dried to reach a predetermined lower water content.

3. The process according to claim 1, wherein said polyol is selected from the group consisting of a polyester polyol, a polyacrylate polyol, a polyurethane polyol, a polycarbonate polyol, a polyether polyol, a polyesterpolyacrylate polyol, a polyurethane polyacrylate polyol, a polyurethane polyester polyol, a polyurethane polyether polyol, a polyurethane polycarbonate polyol, and a polyester polycarbonate polyol, or a mixture thereof.

4. The process according to claim 1, wherein the initial thickness of the foam layer as applied on the substrate, i.e. at the beginning of step (ii) is from 100 µm to 8 mm.

5. The process according to claim 1, wherein said "predetermined point" in time in step (iv) is reached (A) when the thickness of the foam has increased by at least 60% vis-à-vis the thickness of the layer as initially applied in step (ii), or
   (B) when the peak temperature of foam curing has been reached, or
   (C) when the temperature of the foam layer is in the range from 25° C. to 35° C., after the temperature had been in the range of from 18° C. to 24° C. at the beginning of step (iii).

6. The process according to claim 1, wherein said "predetermined location" along the production line in step (iv) is 5 m or more from the point in the production line at which the mixture from step (i) is applied onto the substrate.

7. The process according to claim 1, wherein the maximum temperature reached by way of the accelerated curing of step (iv) is controlled to be in the range of from 30° C. to 95° C.

8. The process according to claim 2, wherein the maximum temperature or average temperature, is lower in the drying step (v) than in the accelerated curing step (iv).

9. The process according to claim 1, wherein the foam resulting after step (iv) or after step (v) is an open cell foam.

10. The process according to claim 1, wherein the accelerated curing of step (iv) is achieved by infrared heating with 2 or more infrared lamps.

11. A medical dressing comprising a foam produced from the process according to claim 1.

12. The medical dressing according to claim 11, wherein said medical dressing further comprises at least one further layer.

13. The process according to claim 1, wherein said "predetermined point" in time in step (iv) is reached 2 to 10 minutes after the beginning of step (iii).

14. The process according to claim 1, wherein said "predetermined point" in time in step (iv) is reached once a given volume segment of the foam layer has reached a degree of curing of from 50% to 90%.

* * * * *